United States Patent
Xin et al.

(10) Patent No.: US 9,417,132 B2
(45) Date of Patent: Aug. 16, 2016

(54) MULTISPECTRAL IMAGING COLOR MEASUREMENT SYSTEM AND METHOD FOR PROCESSING IMAGING SIGNALS THEREOF

(75) Inventors: Haozhong Xin, Hong Kong (CN); Sijie Shao, Hong Kong (CN); Huiliang Shen, Hong Kong (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 623 days.

(21) Appl. No.: 13/882,508

(22) PCT Filed: Aug. 24, 2011

(86) PCT No.: PCT/CN2011/078862
§ 371 (c)(1),
(2), (4) Date: Jul. 19, 2013

(87) PCT Pub. No.: WO2012/058977
PCT Pub. Date: May 10, 2012

(65) Prior Publication Data
US 2013/0293702 A1 Nov. 7, 2013

(30) Foreign Application Priority Data

Nov. 11, 2010 (CN) .......................... 2010 1 0539818

(51) Int. Cl.
*G01J 3/52* (2006.01)
*G01J 3/02* (2006.01)
(Continued)

(52) U.S. Cl.
CPC ................. *G01J 3/52* (2013.01); *G01J 3/0208* (2013.01); *G01J 3/0216* (2013.01); *G01J 3/0235* (2013.01);
(Continued)

(58) Field of Classification Search
CPC ................. G01J 2003/1226; G01J 2003/2826; G01J 3/0208; G01J 3/0216; G01J 3/0235; G01J 3/10; G01J 3/28; G01J 3/51; G01J 3/52; G01J 3/524; G01N 2021/1776; H04N 9/73
See application file for complete search history.

(56) References Cited

U.S. PATENT DOCUMENTS 3,762,817 A * 10/1973 Harklau ........................ 356/73
5,850,472 A * 12/1998 Alston et al. .................. 382/162
(Continued)

FOREIGN PATENT DOCUMENTS

CN        1363826 A    8/2002
JP        2005-265752    9/2005

OTHER PUBLICATIONS

International Search Report & Written Opinion of PCT/CN2011/078862 dated Dec. 8, 2011.
(Continued)

*Primary Examiner* — Peter D Le
(74) *Attorney, Agent, or Firm* — Ella Cheong Hong Kong; Sam T. Yip

(57) ABSTRACT

A multispectral imaging color measurement system, comprising a dark room, a sample platform and an imaging device for capturing said object being measured; a controllable illumination device, a filter wheel unit, an imaging signal processing unit and an electronic control unit. A method for processing imaging signals of the multispectral imaging color measurement is also proposed. The multispectral imaging color measurement system and the method for processing imaging signals thereof can overcome the inaccuracy of traditional digital imaging systems and the limits of spectrophotometer systems and provide users in the textile industry with highly accurate color measurement and evaluation.

13 Claims, 10 Drawing Sheets

(51) Int. Cl.
  *G01J 3/10* (2006.01)
  *G01J 3/51* (2006.01)
  *H04N 9/73* (2006.01)
  *G01J 3/12* (2006.01)
  *G01J 3/28* (2006.01)
  *G01N 21/17* (2006.01)

(52) U.S. Cl.
  CPC .... *G01J 3/10* (2013.01); *G01J 3/28* (2013.01); *G01J 3/51* (2013.01); *G01J 3/524* (2013.01); *H04N 9/73* (2013.01); *G01J 2003/1226* (2013.01); *G01J 2003/2826* (2013.01); *G01N 2021/1776* (2013.01)

(56) References Cited

U.S. PATENT DOCUMENTS

| | | | | |
|---|---|---|---|---|
| 6,449,004 | B1* | 9/2002 | Okisu et al. | 348/44 |
| 7,079,251 | B2 | 7/2006 | Millerd et al. | |
| 2002/0122192 | A1 | 9/2002 | Ott | |
| 2004/0066515 | A1* | 4/2004 | Ott | 356/418 |
| 2004/0178370 | A1* | 9/2004 | Oldham et al. | 250/559.4 |
| 2005/0083531 | A1 | 4/2005 | Millerd et al. | |
| 2005/0219659 | A1 | 10/2005 | Quan | |
| 2006/0050277 | A1 | 3/2006 | Ok et al. | |
| 2007/0161876 | A1* | 7/2007 | Bambot et al. | 600/310 |
| 2008/0128593 | A1 | 6/2008 | Nakaya et al. | |
| 2009/0180684 | A1* | 7/2009 | Tani | 382/162 |
| 2010/0092083 | A1 | 4/2010 | Herloski et al. | |
| 2010/0242768 | A1 | 9/2010 | Huber | |

OTHER PUBLICATIONS

Diwan Ariana et al., Intergrating multispectral reflectance and fluorescence imaging for defect detection on apples, computers and electronics in agriculture, vol. 50 (2006), p. 148-161.

Martin A. Hunt, Imaging tristimulus colorimeter for the evaluation of color in printed textiles, Proceedings of SPIE International Society for optical Engineering, US, vol. 3652, Jan. 1, 1999, p. 118-128.

European Search Report issued on Aug. 12, 2015.

Office Action from SIPO issued on Sep. 16, 2013.

* cited by examiner

MULTISPECTRAL IMAGING COLOR MEASUREMENT SYSTEM AND METHOD FOR PROCESSING IMAGING SIGNALS THEREOF

CROSS REFERENCE TO RELATED APPLICATION

The present application is a national phase application of PCT/CN2011/078862 filed on Aug. 24, 2011 claiming priority of CN201010539818.2 filed on Nov. 1, 2010, and the disclosures of which are hereby incorporated by reference in their entirety.

FIELD OF THE INVENTION

The present invention relates to imaging field, particularly relates to a multispectral imaging color measurement system and method for processing imaging signals thereof.

BACKGROUND

Currently, spectrophotometer can be used to carry out color measurement on large monochrome objects with high accuracy. However, as spectrophotometer has a very low spatial resolution, it cannot be used to measure various types of textile and apparel samples, for example, yarn dyed fabric, lace, textile accessories and printed fabric.

Conventional imaging devices, including digital cameras and color scanners, record color information by passing surface reflected light through a plurality of color filters having different spectral transmittance, and forming images from the reflected light by an electronic sensor. Conventional devices are associated with various advantages for measuring many colors at the same time. They are most commonly used in measuring small, multicolor objects and capturing color information on surface of an object having a complicated texture. However, in one aspect, the traditional primary color and colorimetric imaging systems, due to violation of the Luther Rule, are difficult to produce color images of high accuracy. The Luther Rule refers to spectral sensitivity of most cameras that is not similar to human eyes or linear combination of human eyes. Furthermore, the conventional colorimetric imaging systems can only output tristimulus values, which lead to metamerism errors caused by different observers and different lighting systems. Therefore, these conventional colorimetric measurement systems, such as DigiEye produced by Verivide Corp., do not satisfy the high color quality requirements in textile and apparel industry.

SUMMARY OF THE INVENTION

The present invention provides a multispectral imaging color measurement system and method for processing imaging signals thereof with high accuracy to overcome the low accuracy problem of conventional color measurement systems in textile and apparel industry.

Below is the technical solution provided in the present invention to solve the technical problem:

The present multispectral imaging color measurement system comprises a dark room forming an enclosed space for multispectral imaging, a sample platform located in said dark room for laying and fixing an object being measured, an imaging device located in said dark room for capturing said object being measured, a controllable illumination device, a filter wheel unit, an imaging signal processing unit and an electronic control unit.

The controllable illumination device is located in the dark room, which comprises at least one lighting tube configured to be arranged symmetrically above the object being measured while pointing towards the object being measured.

The filter wheel unit is located between said imaging device and said object being measured, which is for filtering light emitted from said controllable illumination device and reflected by said object.

The imaging signal processing unit is located within said imaging device for calibrating and reconstructing reflectance of images captured by said imaging device.

The electronic control unit has communication connection with said controllable illumination device, said filter wheel unit and said imaging device, for controlling said controllable illumination device, filter wheel unit and imaging device when they are in operation.

The lighting tube of the present multispectral imaging color measurement system comprises light sources that are connected sequentially, an optical integrated column for collecting maximal uniform light, a series of lenses for further improving lighting uniformity and degree of magnification, a photo-resistant plate for reducing diffused light, wherein internal part of said lighting tube is coated with a light-absorbing material for reducing internal diffused light.

The light sources may be a halogen tungsten lamp with a smooth curve of spectral energy distribution, powered by two high-precision DC power supply.

The optical integrated column is in a hollow horn-like structure surrounded by a glass wall.

The series of lenses comprises an optical grating for limiting light beam edges, and one or more convex lenses and concave lenses having different refractive indexes.

The photo-resistant plate is placed on the front edge of said series of lenses.

The filter wheel unit of the present color measurement system comprises a step motor, a filter wheel and a belting device connecting said step motor and said filter wheel.

The step motor provides said filter wheel with power and signal for selecting position of filters; said step motor is controlled by said electronic control unit.

The filter wheel comprises a chassis. Said chassis has one or more slots and one or more holes for reducing rotational mass. The filters are fastened in said one or more slots by upper retaining rings, and the filter wheel further comprises a built-in infrared optical switch for position detection.

The belting device comprises a first synchronizing wheel mounted on rotating shaft of said step motor, a second synchronizing wheel mounted on shaft of said chassis, and a belt of said belting device meshes outer edges of the first and second synchronizing wheels.

The imaging device of the present color measurement system comprises a CCD sensor or a CMOS sensor. Said sensor comprises a built-in A/D converter for converting light signal of selected wavelength into digital signal in order to generate multi-channel spectral images, wherein said light signal of selected wavelength is selected by the filter wheel and is projected to focal plane of said sensors.

The electronic control unit of the present color measurement system comprises: an illumination device control unit for adjusting a set value of voltage and current of a power supply for said illumination device to keep a steady operation of the light sources; a microprocessor module for controlling acceleration, steady driving and deceleration of said step motor; an interface circuit board which provides communication between said imaging system, illumination device control unit and filter wheel unit.

The present invention also provides an imaging signal processing method comprising correcting geometric error caused by optical lenses or filters and correcting brightness of imaging signal in each optical channel. The present method further comprises estimating an exposure time of linear working range of a sensor, wherein said sensor converts incident light signal into digital imaging signal within said exposure time; correcting image noise caused by inherent noise source in said sensor; calibrating multi-channel images in the optical channels that are captured through different filters to eliminate offset of content caused by relative misaligned position of the filters in the filter wheel unit, differences in refractive indexes in the filters, a slight objective distance shift between the filters in the filter wheel unit and the object being measured; correcting overlapping images caused by overlapping effect in each channel.

The present method further comprises reconstructing reflectance of the imaging signal, thereby generating a spectral reflectance image of said object being measured.

In the method for processing imaging signals of the present invention, the inherent noise source comprises a dark current. $I_{Corr}$ represents a corrected image, $I_{rep}$ represents an initial or original image without correction, $I_{Dark}$ represents a "dark current" image, $I_{white}$ represents a uniform white target image, coefficient k is a calibration constant to guarantee that CCD sensor operates under the linear range, and the calibration process is represented by the following formula:

$$I_{Corr}(i, j) = k \frac{I_{rep}(i, j) - I_{Dark}(i, j)}{I_{white}(i, j) - I_{Dark}(i, j)}.$$

In the present method for processing imaging signals, said calibrating multi-channel images in the optical channels that are captured through different filters further comprises selecting an image in a channel as a reference channel image, calibrating images in other target channels according to the selected reference channel image, conducting a binary preprocessing of the calibrated images collected from each channels, followed by extracting characteristic edges of said calibrated images collected from each channel using an edge detection algorithm; dividing said reference channel image and the target channel images into a series of local regions, selecting a minimum value of an error cost function of spatial displacement, and determining a maximum correlation coefficient of distortion vector in each local region according to a gradient descent algorithm.

The present method further comprises conducting a bilinear interpolation in the target images, except for the edges thereof, to generate offset vectors of pixels in the local regions, combining said offset vectors of pixels in the local regions with offset vectors of the edges of corresponding local regions to generate a group of offset vectors having the same magnitude as those of the original image in the selected local region, thereby generating a mapping function f (x).

Calibration of said target channel images is then resumed in accordance with the mapping function f(x).

In the present method for processing imaging signals, said correcting of overlapping images caused by overlapping effect in each channel further comprises extracting white objects by using an image threshold process; matching each pixel of the entire image with template by scanning in order to determine position of overlapping images caused by overlapping effect; eliminating the overlapping effect according to corresponding parameters for overlapping images of each imaging channel.

In the present method for processing imaging signals, said reconstructing signal reflectance of the imaging signal comprises using Wiener Estimation Method or Pseudo Inverse Calibration to reconstruct the reflectance.

The present multispectral imaging color measurement system and method for processing imaging signals thereof having the following advantages: the present multispectral imaging color measurement system overcomes the inaccuracy of traditional digital imaging systems and the limits of spectrophotometer systems. The use of uniform illumination in the present multispectral imaging color measurement system and the method for processing imaging signals provide an integrated multispectral imaging color measurement system (ICM) that is useful in color measurement and color quality control in the textile industry. The present invention is incorporated with an uniform illumination device which provides an uniform imaging environment and with an imaging signal processing system for synchronously capturing of spectral color images with high spatial resolution. The present invention is capable of measuring multiple colors regardless of the number of colors being measured. The present invention is advantageous over spectrophotometer on the provision of structural information of objects, and also advantageous over the current digital camera system on capturing true spectral reflectance and eliminating metamerism under different light sources.

BRIEF DESCRIPTION OF THE DRAWINGS

Below is a more detailed description of the present invention in combination with the accompanying figures and embodiments.

DETAILED DESCRIPTION OF THE INVENTION

Figure 1:
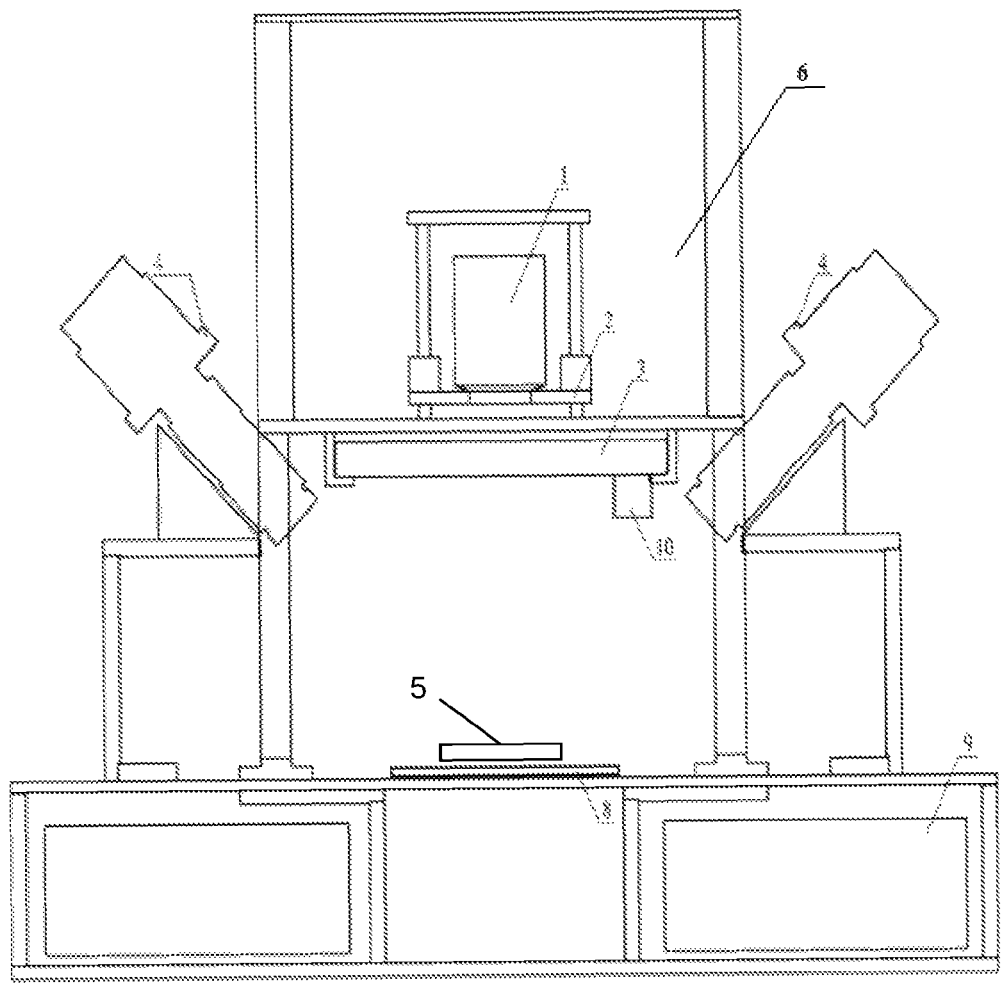
FIG. 1 is a schematic view of imaging color measurement system according to an embodiment of the present invention.

FIG. 1 is a schematic view of imaging color measurement system according to an embodiment of the present invention. As shown in FIG. 1, to avoid the interference of light from external environment on color measurement, all imaging components are configured in Dark Room 6. White Board 5 and object being measured are placed under a pair of symmetrical Lighting Tubes 4 tiled at an angle of 45±5° to White Board 5. To attain an uniform distribution of light intensity, a controllable illumination device is specially designed. Imaging Device 1, Filter Wheel 3 and Lens 2 are configured at upper part of the measurement system for obtaining multispectral imaging of the object being measured. Narrow bandpass interference filter is one example of filters suitable for use in multispectral color measurement system of the present invention.

Figure 2:
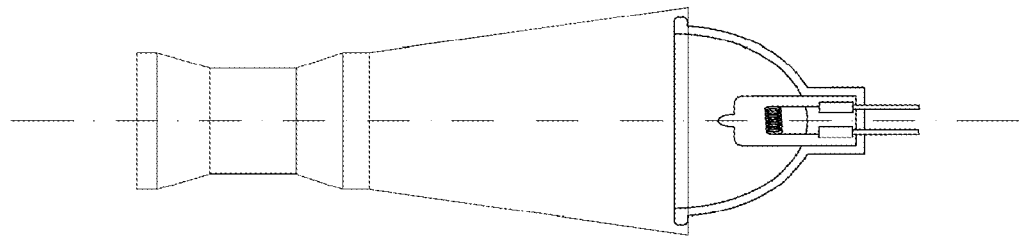
FIG. 2 is a schematic view of lighting tube according to an embodiment of the present invention.

FIG. 2 is a schematic view of lighting tube according to an embodiment of the present invention. Each lighting tube comprises three units, e.g. a light source, an optical integrated column and a series of lenses. Halogen tungsten lamp can be used as the light source. The light source emits continuous light having a spectral power under concentrated distribution within a wavelength range of visible light and a stable light intensity within a specific time. The optical integrated column is used to gather as much light as possible, which can generate uniformly diffused reflected light at outlet of the optical integrated column, and uniformity and magnification of illumination of said reflected light within an effective range can be further improved by the series of lenses. Finally, uniform illumination region provides a desired multispectral imaging color measurement system.

High pressure xenon lamp can also emit continuous spectrum, and generally keeps colour temperature of 5000 k. The combination of suitable conversion filter with xenon lamp can simulate a D65 standard illuminant. However, like all other gas-discharge light sources, a xenon lamp has specific emission line spectrum with a wavelength of approximately 475 nm. To reduce the effects of this specific line spectrum, usually special filters are used to control emission spectrum. Comparatively, the relative spectral energy distribution of halogen tungsten lamp is a smooth curve without peak or minor vibration. In the present invention, halogen tungsten lamp is used as a light source to provide multispectral imaging color measurement system with a continuous light spectrum distribution.

As a light source of the present multispectral imaging color measurement system, stability of plane light source is the first criteria to capture high quality images. Two high-precision DC stable power sources provide halogen tungsten lamp with constant voltage and current, so as to guarantee light intensity of light source is steady. Wired or wireless interface is used for connecting DC stable power sources and a host system. The host system sends an instruction through suitable wired or wireless connection protocol, to modulate a required voltage and current values in accordance with set value for keeping light sources to operate under a stable operation state.

In addition, to further reduce the effects of light path and diffused light in lighting tubes, each lighting tube further comprises photo-resistant plate. The photo-resistant plate locates at the front edge of each series of lenses, to reduce diffused light on the surface of the object under illumination. To further reduce diffused light, the internal part of lighting tube can be coated with light-absorbing materials.

Figure 3:
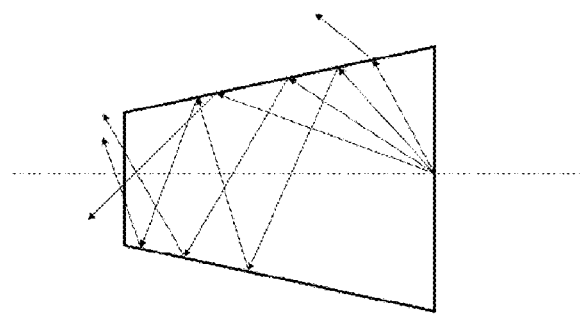
FIG. 3 is a schematic view of optical integrated column according to an embodiment of the present invention.

FIG. 3 is a schematic view of optical integrated column according to an embodiment of the present invention. As shown in FIG. 3, light from the halogen tungsten lamp being reflected multiple times is regarded as a point light source with certain scale and high brightness. The brightness distribution of said point light source is similar to a non-uniform Gaussian distribution. To provide uniform illumination conditions within 20 cm×20 cm area required in the present multispectral imaging color measurement system, further treatment on said reflected light is required. The present invention includes an important optical instrument for light guiding, i.e. the optical integrated column. The main function of the optical integrated column is to collect more uniform light.

The integrated column of the present invention is an hollow structure surrounded by optical glass lens, for homogenizing emitted light. The hollow structure maximizes the amount of light that can be collected, for example, for capturing planar diffusive reflected light on the left side of optical integrated column. When a spread angle of a light beam guided into integrated column is smaller than an aperture angle of the light beam, the light beam having reflected multiple times inside the optical glass lens emits from the outlet of the integrated column. When the spread angle of light beam is larger than the aperture angle of light beam, said light beam becomes refracted. Through this light guiding mechanism, light emitted from the outlet of the integrated columns has greater uniformity, and the direction of emission at this time is disordered. Aperture angle of light refraction tube is determined by the refraction coefficient thereof.

Figure 4:
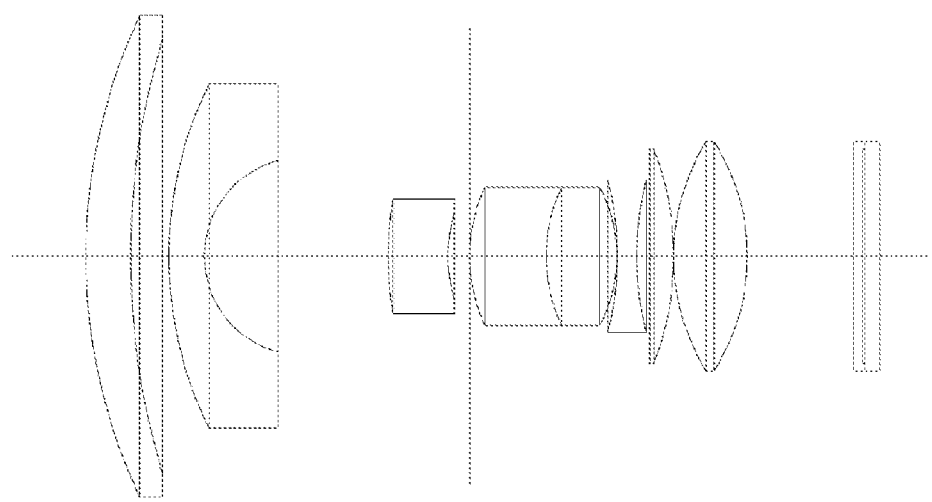
FIG. 4 is a schematic view of the series of lenses according to an embodiment of the present invention.

FIG. 4 is a schematic view of the series of lenses according to an embodiment of the present invention. Although the light having had reflected multiple times inside the inner glass walls of the optical integrated column are uniform, these light being within the effective range of an uniform illumination area remains relatively small, which cannot meet the requirements of a multispectral imaging color measurement system to measure large scale of planar uniform illumination area. Therefore, the present invention comprises a series of lens for expanding uniform illumination area of the light emitted from optical integrated column. To guarantee magnification coefficient of the series of lenses, and to reduce optical distortion, lens aberration and chromatic aberration, multiple pieces and types of lenses are used in the series of lenses of the present invention, whose light path diagram is shown in FIG. 4.

The series of lenses of an embodiment of the present invention comprises two series of lenses. The first series comprises five lenses, wherein two are concave lenses and three are convex lenses. A second series comprises one concave lens and one convex lens. The combination of concave lenses and convex lenses can eliminate geometric distortion of lenses. The selection of lenses with different refractive indexes eliminates dispersion errors. As shown in FIG. 4, the main function of optical grating in the series of lenses is to prevent the edge of light beam from projecting outside of the series of lenses. Generally, the distortion of light beam is more serious than the distortion caused by change in position of lens. Said optical grating can effectively enhances uniformity and contrast ratio of the screen's brightness, while restricting the utilization rate of light source at the same time.

Figure 5:
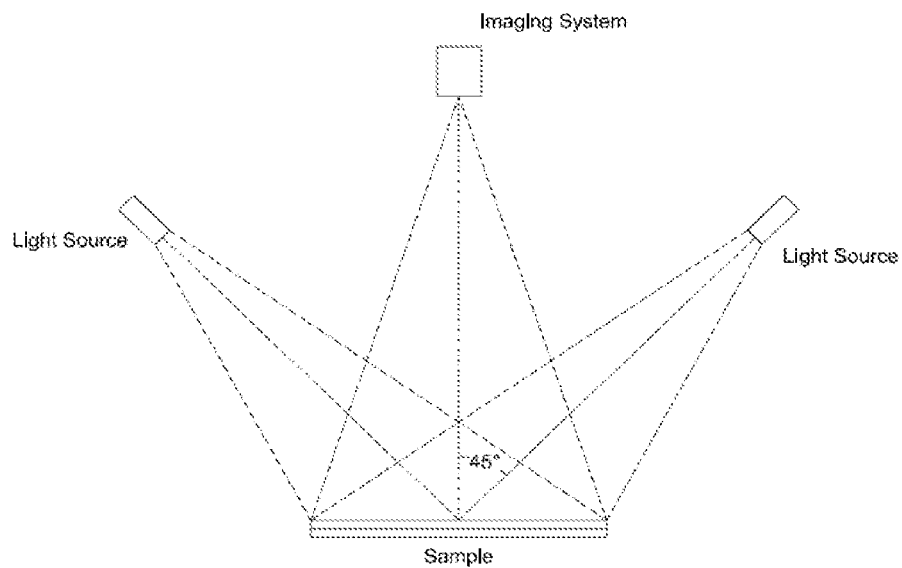
FIG. 5 is a schematic view of symmetrical illumination device comprising two lighting tubes according to an embodiment of the present invention.

FIG. 5 is a schematic view of symmetrical illumination device comprising two lighting tubes according to an embodiment of the present invention. As shown in FIG. 5, the two lighting tubes are tilted at an angle of 45±5° to a symmetrical plane thereof. Although the illumination devices in FIG. 1 and FIG. 5 apply two symmetrical lighting tubes, but the number lighting tube is not confined to two. In another embodiment of the present invention, a circumferential illumination device may comprise any suitable light sources such as halogen tungsten lamp of any quantities or combination. In addition, the illumination device may comprise light sources of any number of layers so as to generate an uniform illumination area.

Figure 6:
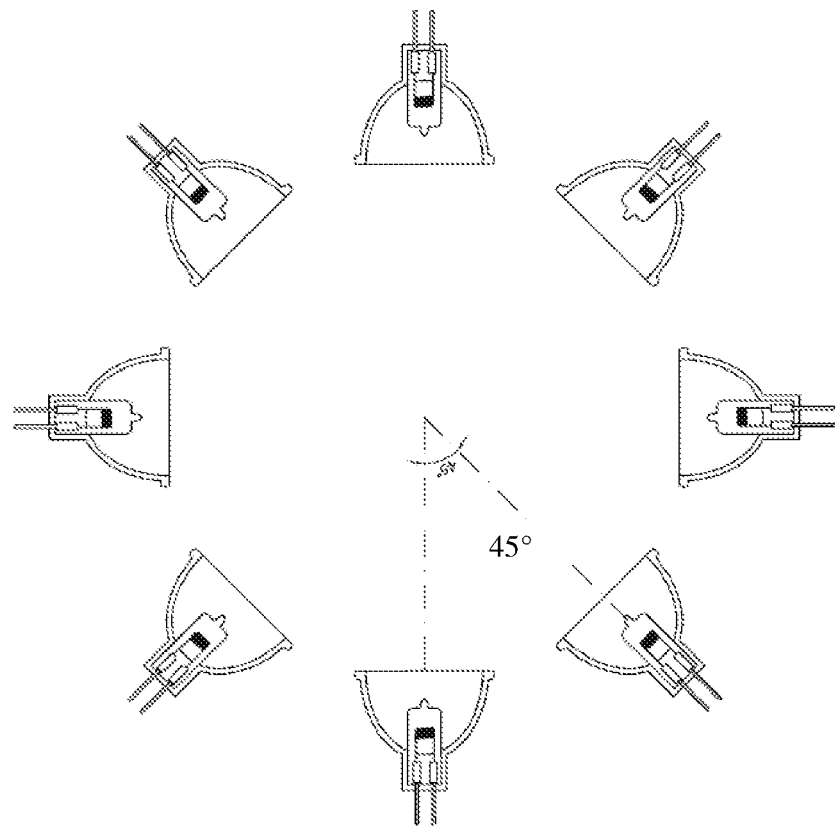
FIG. 6 is a schematic view of circumferential illumination device comprising eight light sources distributed evenly at an angle of 45° between each two light sources according to another embodiment of the present invention.

For example, FIG. 6 shows a schematic view of a circumferential illumination device according to another embodiment of the present invention. As shown in FIG. 6, eight light sources with an angle of 45° respectively are uniformly distributed.

Figure 7A:
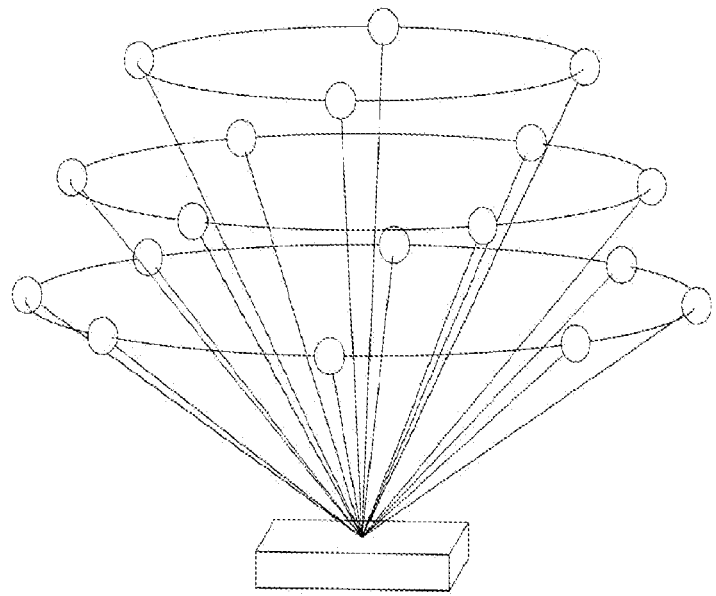
FIG. 7A is a schematic view of illumination device with a multilayered structure according to another embodiment of the present invention.
Figure 7B:
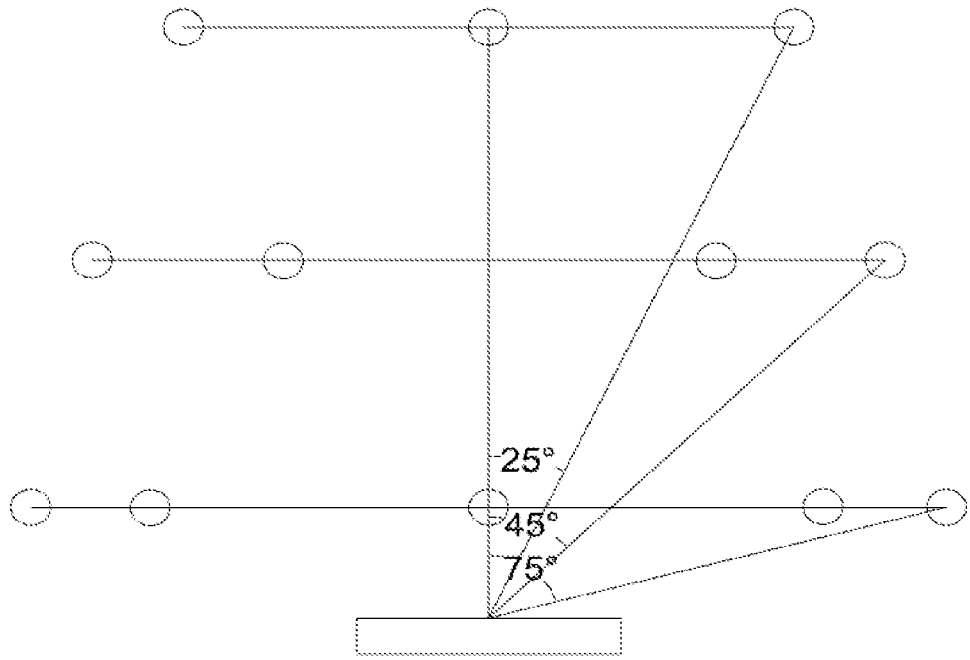
FIG. 7B is a schematic view of intersection angle of multilayered illumination device according to another embodiment of the present invention.

FIG. 7A and FIG. 7B further show a schematic view of illumination device with a multilayered structure. Each light source on each layer of FIG. 7 is arranged in the form of a ring. Each layer of this multilayered circumferential illumination device can work independently. Multilayered circumferential illumination device can illuminate the object being measured from different angles so as to obtain more accurate spectral analysis on the object with a directional textured pattern and on other colors which depend on effects of different angles of incidence.

Figure 8:
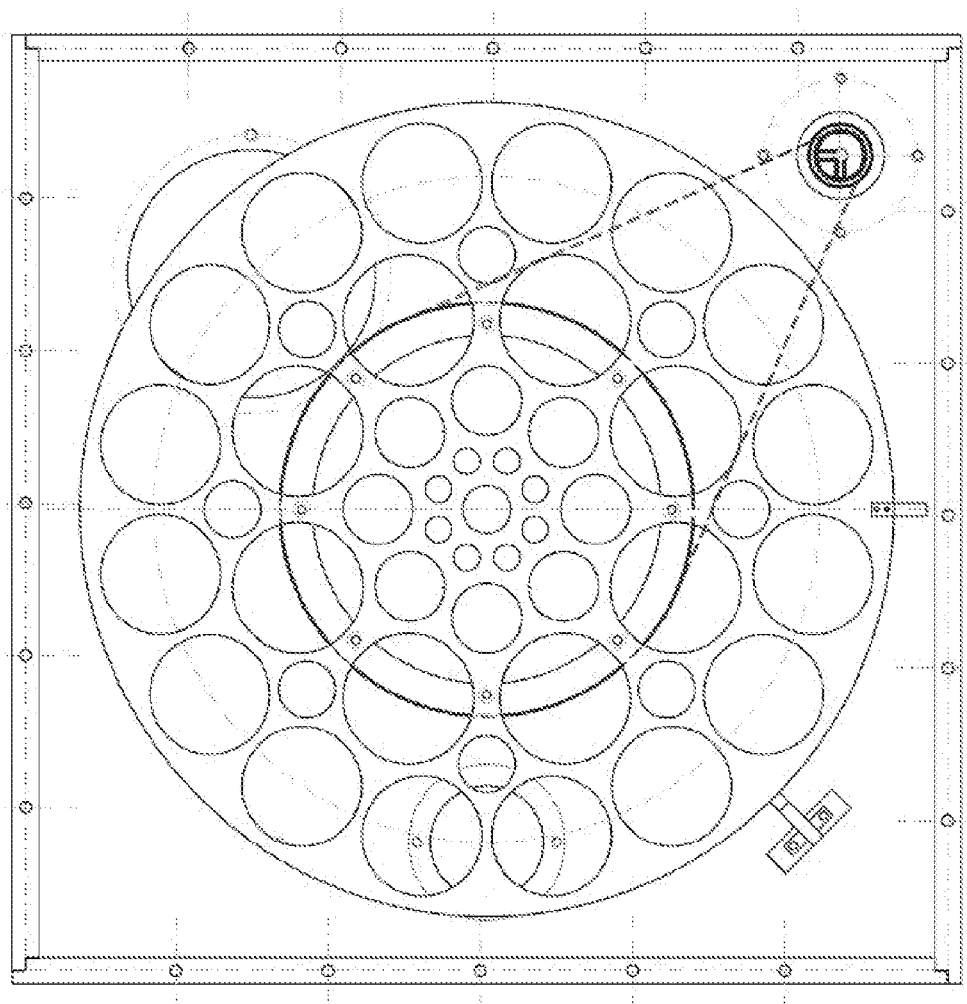
FIG. 8 is a schematic view of filter wheel unit according to an embodiment of the present invention.

FIG. 8 is a schematic view of a filter wheel unit according to an embodiment of the present invention. As shown in FIG. 8, the filter wheel unit comprises many narrow bandpass filters mounted on tooth of the wheel in a continuous tight arrangement. These narrow bandpass filters having various central wavelength allow light with different range of wavelengths to pass through corresponding filters. For example, different areas of said filters can filter light into different spectrum with wave width of 10 or 20 nm. Specifically, different areas of said filters can filter the light into different spectrum with wave width of 20 nm centering on 400 nm, 420 nm, 440 nm, 460 nm, 480 nm, 500 nm, 520 nm, 540 nm, 560 nm, 580 nm, 600 nm, 620 nm, 640 nm, 660 nm, 680 nm and 700 nm respectively. In this invention, the number of filters is not confined to 16 or 31, and band width of filters is not confined to 20 nm or 10 nm.

FIG. 8 shows an embodiment of the present invention, in which the filter wheel comprises 16 narrow bandpass filters. In one embodiment, the filter wheel is customarily mounted with narrow bandpass filters with various central wavelength to be used between imaging device and the object being measured to collect information in each spectral channel, wherein the imaging device functions as a color analyzer/sensor. Said narrow bandpass filters can provide a spectrum with an appropriate range of wavelengths for spectral analysis and color measurement. For example, narrow bandpass filters with alternative wavelength can provide spectrum with 16 different ranges of wavelengths for detection and analysis, other appropriate number of filters or spectrum is also acceptable.

The filter wheel unit applied in this embodiment comprises a chassis with 16 slots for mounting filters. Each slot comprises an upper retaining ring for fastening the edge of the filters and reducing the inclination of filters when the filter wheel rotates. The filter wheel further comprises a belting device, in lieu of a connecting means, directly connecting to a drive shaft of a step motor for carrying heavy load, and to ensure higher rotation accuracy. A first synchronizing wheel is mounted on rotating shaft of the step motor, a second synchronizing wheel is mounted on the periphery of the wheel chassis with multiple narrow bandpass filters arranged annularly and equally-spaced between center shaft and the periphery thereof. The wheel chassis comprises various holes and cavities for reducing load during rotation. The belting device connects outer edge of the first and second synchronizing wheels to drive the filter wheel chassis to rotate by centering on the first synchronizing wheel.

As shown in FIG. 8, the filter wheel can be a compact circular structure with one end connecting to the step motor. Said filter wheel comprises a built-in infrared optical switch for position detection, which calibrates an initial position of the wheel when the wheel begins to rotate. The step motor is controlled by a microprocessor module, connecting the filter wheel and the host system with wired or wireless interface. The step motor is an external component which provides an electric filter wheel with power source and communication for position selection of filters. In the present invention, two sets of complementary controls are employed to detect rotating speed and position of the filter wheel. The use of an incremental encoder provides reference position for an automatic control. The step motor is usually powered even when it halts, and there is no obvious rebound or position drifting when it is fastened in the slot.

When the wheel rotates, the microprocessor module sends rotating impulse of three working states comprising acceleration, steady driving and deceleration to motor driver, at the same time initiation frequency, driving frequency, acceleration time and deceleration time are set to corresponding predetermined values. At each resting position of the filter wheel, light beam is transmitted at a selected wavelength through filters and optical lens. Then, the light beam is projected to the focal plane of a charge-coupled device (CCD) or a complementary metal oxide semiconductor (CMOS) sensor, CCD or CMOS can convert simulated light signal into digital electrical signal through A/D converter built in the circuit of the imaging sensor. The step motor drives the wheel to rotate continuously and imaging sensor generates spectral images through 16 or more channels.

For convenient communication among the imaging device, the illumination device control unit and the filter wheel, an interface circuit board is configured to support communication media of any appropriate type, for example, wired or wireless network or connection. The interface circuit board may comprise any type which is suitable for communication between the microprocessor module and the host system. For example, a suitable interface circuit board may be one with synchronization mechanism which supports exposure time of a camera or an interface circuit board with continuous positioning connected according to RS232 Communication Protocol to support narrow bandpass filters.

Figure 9:
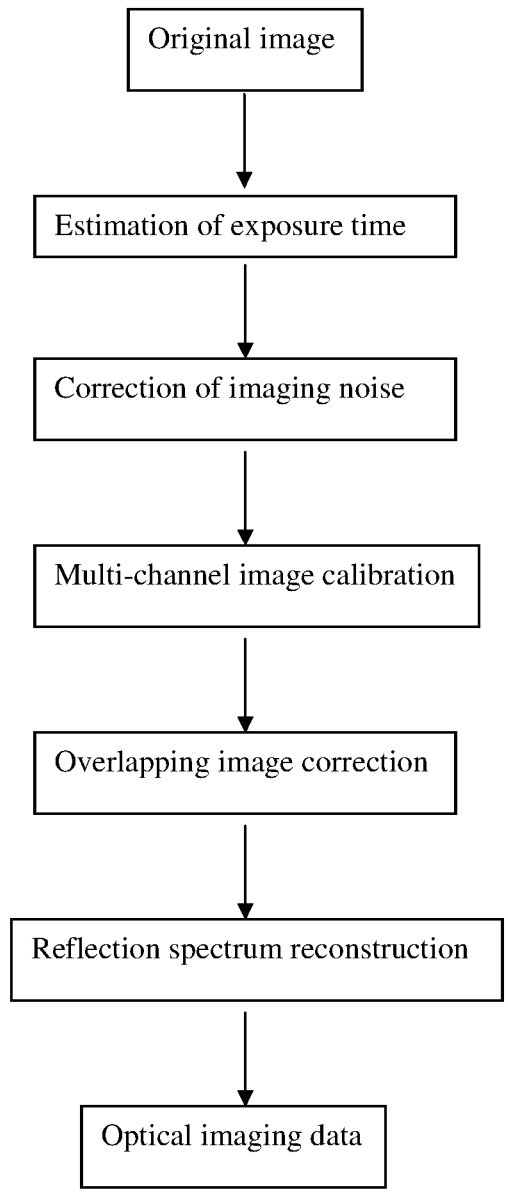
FIG. 9 is a flowchart of a method for processing imaging signals according to the present invention.

FIG. 9 is a flowchart of the method for processing imaging signals in the present invention. As shown in FIG. 9, the method for processing imaging signals converts an original image into optical imaging signals comprises: estimating exposure time, correcting imaging noise, calibrating multi-channel image, correcting overlapping image, correcting image brightness, and reconstructing reflectance. Geometric correction and brightness correction of mobile scene are commonly-used technical means by a skilled in the art in this field, and it will not be specified here.

Each CCD sensor has its maximum operating range, refers to as time of exposure or exposure time herein. Once a maximum input exceeds a threshold value, output signals no longer increase and the sensor is saturated. In addition, said sensor has a minimum response value. Below said minimum response value, the sensor will not make a response. To estimate linear range of an exposure time of CCD sensor in each channel, a white uniform target board is placed on sample platform in the dark room, to estimate a first appropriate value for exposure time of each filter.

The basic method to estimate exposure time is by setting a mean value of image photographing to obtain certain index value s, which is close to maximum probable value or saturation value of signals (e.g. the value is 16384 at 14-digit quantization). However, to avoid saturation or over-saturation in collecting images, a safe range will be set for index value s. For example, multiplication correction coefficient e.g. 0.75 is usually used for estimating exposure time of each channel.

Figure 10:
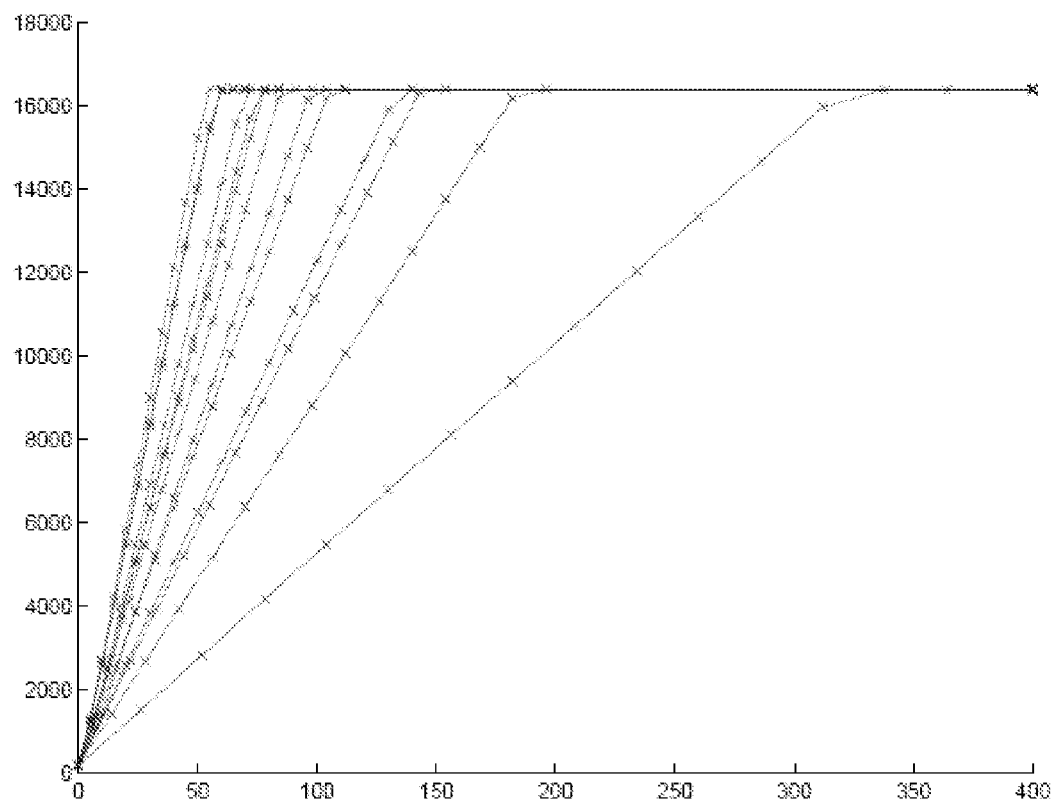
FIG. 10 is a graph showing relationship between average response value of image capturing in each channel and respective exposure time.

FIG. 10 is a graph showing a relation between average response value of photographing in each channel and respective time of exposure. As shown in FIG. 10, various different estimated maximum time intervals between 35 ms and 340 ms are used to guarantee CCD sensor work in linear dynamic range.

Technically speaking, CCD must execute four steps in the process of image generation, comprising: charge generation, charge collection, charge transfer and charge measurement. The charge generation of each pixel is proportional to current level of incident light, therefore all pixels generates a spatial sample representative of a continuous image. In the process of charge collection, after electrons are generated, CCD sensor will conduct accurate reproduction of images. The reproduced digital images comprise each pixel in electron charge mode, which is presented by digital data of electron stored during the period of integration. When no light reaches to the detector of CCD, an incremental transfer of charges in each pixel occurs. Finally, during charge measurement, charges of each pixel are connected to output amplifier and then digitalized in order to pass through analog-digital conversion (ADC).

During image generation, inherent noise sources in imaging device (e.g. CCD camera) will change digital level corresponding to each pixel, result in distortion of true image, reduction of radiation accuracy, image quality and resolution ratio.

In the present invention, the most significant noise source is a dark current.

The generation of dark current noise is a thermal process, in which electrons absorb heat and jump to an intermediate state, i.e. being motivated to enter a guiding zone. For this reason, the most effective method to reduce dark current is to cool CCD. In the present invention, CCD sensor works at −30° C. A cooling system is incorporated in the lighting tube to reduce surrounding temperature, and sustain a stable state in the multispectral imaging color measurement system.

Although a decrease of fluctuation of lighting intensity in the hardware component can greatly improve repeatability of light source, a stable and uniform light source is another important factor to capture high quality images for photometric measurement. Non-uniform incidence light source leads to minor changes on pixel response of image system within visual range, so as to affect the results of color measurement.

Slight difference in the size of the detector and dosage concentration will result in different quantity of dark current generated by each pixel, which is another main cause of non-uniform noise signal generation in dark current. In multispectral imaging color measurement system of the present invention, not all the pixels in CCD sensor have the same light sensitivity. Even minor changes on thickness of silicon wafer will affect its sensitivity. In addition, although a controllable illumination environment is provided, due to light loss in optical lens, the light reflecting on the sensor may not be uniform. As such minor changes resulting from the change on brightness of the objects themselves cannot be detected, these unnecessary pixels or illumination changes will influence to a certain extent the precision of multispectral imaging color measurement system. The above two types of spatial inhomogeneity jointly causes inhomogeneity of corresponding space in the imaging device (e.g. CCD camera). It is required to correct said spatial inhomogeneity so as to make the imaging device based on CCD camera achieving high-precision range or photometric measurement.

To correct said dark current, dark images are photographed in a dark background or having a closed shutter or a combination thereof, to eliminate non-uniform noises of dark current generated by exposure time of dark images to match white target images. In this case, spatial non-uniformity on image illumination and equipment response result in non-uniform images. The basic process of calibration can be represented in the equation below:

$$I_{Corr}(i, j) = k \frac{I_{rep}(i, j) - I_{Dark}(i, j)}{I_{white}(i, j) - I_{Dark}(i, j)}$$

Wherein, $I_{Corr}$ represents the corrected image, $I_{rep}$ represents the initial or original image without correction, $I_{Dark}$ represents the "dark current" image, $I_{white}$ represents uniform white target image, the coefficient k is a calibration constant to guarantee that CCD sensor operates in a linear range.

A monochrome CCD camera with a filter wheel mounted at the front is used to capture multispectral images, and different refraction coefficient of filters leads to certain offset in the images of different light channels.

To calculate spatial displacement of images between the reference channel and other channels, collect the image of an object being corrected (e.g. black & white checker) in the dark room. In the images of these channels, select the image of an appropriate channel as the reference image, e.g. the image in the channel with wavelength of 560 nm. The matching and correction of images in all the other channels is compared with the selected images in reference channel.

Multi-channel image calibration algorithm is used for capturing multispectral calibration images of object being measured. The images of all other channels are calibrated according to selected images in reference channel. To accurately calculate spatial displacement of local areas in various channels, the first step is to select an appropriate threshold value for binarization processing according to the distribution of gray scale histogram of the images, then using the method of edge detection to conduct gradient screening for multispectral images in local areas. As all the local areas of multispectral images maintain a characteristic edge, edge screening on the input images provides robust within a range of wave length.

Figure 11A:
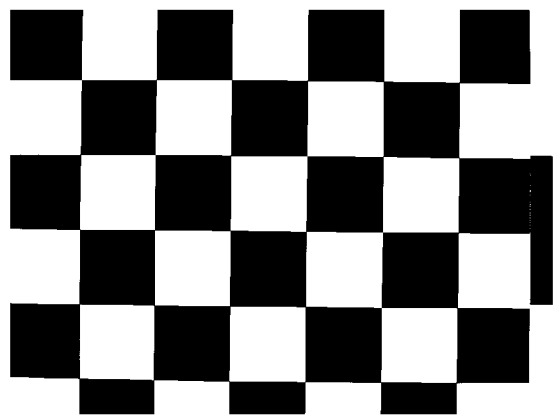
FIG. 11A is a reference channel image in multi-channel image calibration.
Figure 11B:
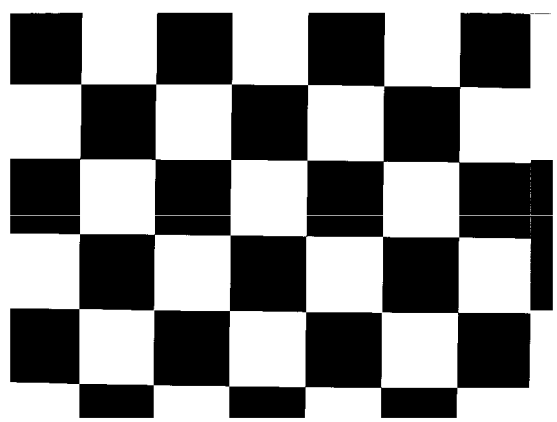
FIG. 11B is a target channel image in multi-channel image calibration.

FIG. 11 shows the steps of the calibration method for multi-channel images: the image being measured is a black & white checker, FIG. 11A is the reference channel (with wave length of 560 nm) image; FIG. 11B is the target channel (with wave length of 700 nm) images. FIG. 11C is the offset between reference channel images and target channel images before the process of multi-channel image calibration; FIG. 11D is the offset between reference channel image and target channel images after the process of multi-channel image calibration. It can be seen that the offset is reduced significantly after calibration.

Figure 11C:
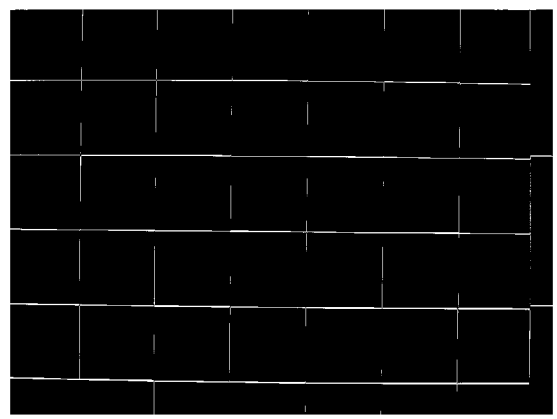
FIG. 11C is a schematic view of offset between the reference channel image and target channel image before multi-channel image calibration.
Figure 11D:
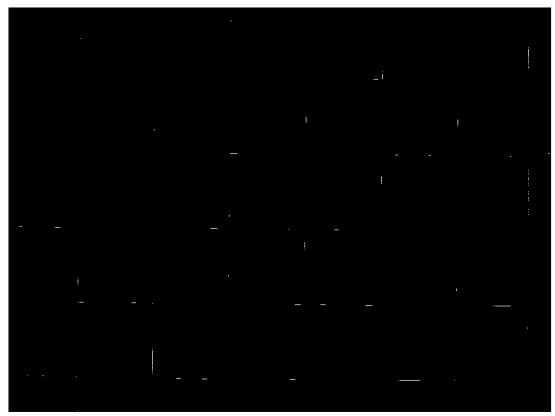
FIG. 11D is a schematic view of offset between the reference channel image and target channel image after multichannel image calibration.

As shown in FIG. 11C, geometric distortion in horizontal direction x and vertical direction y is neither spatial constant in a certain channel nor spatial constant of images of different objects in the same channel. In fact, the geometric distortion depends on the distance of objects, camera zoom and aperture of the camera, therefore, for every multispectral exposure, the software must be calibrated again. To this end, reference image and target images are divided into a series of partitions, so as to consider non-uniformity for distortion vector of images, which is calculated in each respective partition.

The aim of multispectral image calibration is to generate mapping function f: x→x', convert space coordinate x of target image T into Coordinate x' of reference image s. In the present invention, the method to select mapping function f is illustrated below: selecting the minimum value of an error cost function of spatial displacement, calculating the maximum correlation coefficient between the edge of target image and corresponding part of reference image. The process for multi-channel image calibration is shown in mathematical formula below:

$$\max_f I(S(f(x), T(x), f))$$

Wherein, I( ) represents the selected cost function. An appropriate algorithm may be used to find maximum correlation coefficient in each partition. Except the spectrum of reference images with 560 nm wavelength, the maximum displacement of the edges of target images and reconstructed images in horizontal and vertical directions is used for recording images in all the other channels. Finally, vector group with the same size as original image is generated. Said vector group comprises distortion vector of selected partition. Bilinear interpolation in the target image, except the edges thereof, is conducted and generates vectors of remaining pixels. In multispectral imaging color measurement system of the present invention, after multi-channel images are calibrated, the offset does not exceed one pixel to achieve excellent spatial discrimination.

Figure 12:
FIG. 12 is a schematic view of non-parallel surface of filters in the imaging color measurement system according to an embodiment of the present invention.

Due to the limitation in design and manufacturing technology, the filters with the effect of light reflection and transmission interference are not ideal optical components for multispectral imaging color measurement system. Although said filters are coated with anti-reflection film, part of incident light are still being reflected on the surface of medium. As shown further in FIG. 12, the two surface media of filter are not coplanar. In addition, one or more times of reflection occur between the filter and series of lenses. Such imperfect optical property leads to undesired dual imaging or overlapping effect in the images obtained.

The overlapping effect in a certain imaging channel is usually different from that in other channels, as this effect is caused by imperfect design and manufacturing technology of the filters. Overlapping effect will inevitably influence the response of imaging device (e.g. camera) in the position of each pixel, and reduce accuracy of color measurement of a multispectral imaging color measurement system. The ratio between overlapping image's brightness and brightness of the object being measured in different channels is also different, generally lower than 2%. This ratio will dramatically degrades photometric and colorimetric accuracy, particularly for objects with low brightness, therefore overlapping effect in each imaging channel should be corrected.

Figure 13:
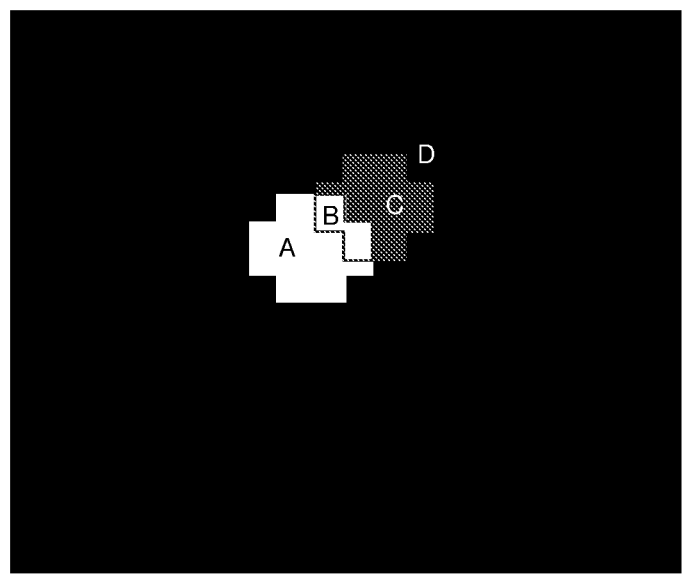
FIG. 13 is a schematic view of overlapping effect according to an embodiment of the present invention.

Brightness ratio and position offset are two important parameters that cause overlapping effect. To determine these two parameters, as shown in FIG. 13, it is possible to conduct imaging processing on a white cross-shaped planar object in a dark background. A skilled artisan would comprehend that the white object is not confined to be cross-shaped, it can be any other shapes. Owing to overlapping effect, except actual object, the image obtained also comprises an overlapping cross with very low brightness, whose position is determined by the process of template matching.

Below is the description of the process for calculating overlapping image parameters and eliminating overlapping effect:

1. Extracting of White Object

The extracting of white object is obtained by image thresholding means. Threshold T is determined by the image's maximum brightness $I_{max}$ and minimum brightness $I_{min}$:

$$T = \frac{I_{max} + I_{min}}{2}$$

Other processes of thresholding can also be used. Pixel with brightness greater than T is considered as a candidate object, and other pixels are considered as background or overlapping image. Due to the influence of image noise, isolated pixel or small partition may be regarded as the candidate object. Once the position of the most probable candidate object is determined, it is feasible to identify part of the image comprising actual object, i.e. template image $I_{template}$.

2. Determining the Position of Overlapping Effect

Figure 14:
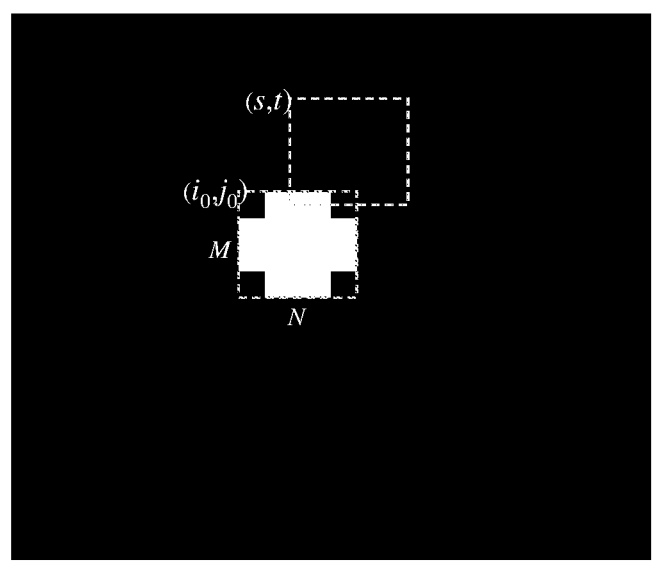
FIG. 14 is a schematic view of template matching process according to an embodiment of the present invention.

FIG. 14 shows the process of template matching to determine the position of overlapping image. The matching process is conducted by scanning the entire image, for example, from the left to the right or from top to bottom. The formula below shows correlation coefficient between the template starting from the position (s,t) and candidate sub-image. It can be seen that, if the pixel (s+m, t+n) is in the range of the object, the pixel will not be calculated as it is the pixel of the object.

$$\eta(s, t) = \frac{\sum_{m=1}^{M}\sum_{n=1}^{N}(I(i_0 + m, j_0 + n) - \bar{I}_{temp})(I(s + m, t + n) - \bar{I}_{cand})}{\left[\sum_{m=1}^{M}\sum_{n=1}^{N}(I(i_0 + m, j_0 + n) - \bar{I}_{temp})^2\right]^{1/2}\left[\sum_{m=1}^{M}\sum_{n=1}^{N}(I(s + m, t + n) - \bar{I}_{cand})^2\right]^{1/2}}$$

The symbols $I_{temp}$ and $I_{cand}$ in the above formula represent mean brightness of the part of object and the part of candidate overlapping image, respectively.

Template matching for each pixel of the entire image is conducted to find position $(s_0, t_0)$ with maximum correlation coefficient. Then calculate the offset of overlapping image according to the formula below:

$$(i_{offset}, j_{offset}) = (i_0 - s_0, j_0 - t_0)$$

Accordingly, brightness ratio of overlapping effect is calculated according to the formula below:

$$\beta = \frac{\bar{I}_C - \bar{I}_D}{\bar{I}_B}$$

wherein, $\bar{I}_B, \bar{I}_C, \bar{I}_D$ are mean brightness of Area B, C and D respectively.

3. Elimination of Overlapping Effect

After the parameters of overlapping effect are obtained, it is feasible to eliminate overlapping effect for any image captured. Below is the calibration density in the position of pixel (i,j):

$$\tilde{I}(i,j)=I(i,j)-\beta \cdot I(i+i_{offset}, j+j_{offset})$$

It should be noted that the parameter $\beta$ and $(i_{offset}, j_{offset})$ refer to a single filter. It is required to conduct elimination of overlapping effect in different imaging channels respectively.

After a series of imaging processing as described above, it is feasible to make use of digital image values with high precision to estimate reflectance reconstruction. The main objective in the process of multispectral reconstruction is to reconstruct spectral reflectance of colored objects with corresponding digital response from imaging device. The process of reflectance reconstruction is usually used for multispectral imaging system, as it needs to collect many spectral channels in the linear model applied to estimate reliable spectral reflectance.

The mathematical methods for spectral reflectance reconstruction comprise interpolation method, e.g. Lagrange polynomial interpolation, cubic spline interpolation, cubic interpolation, discrete fourier transform or modified discrete sine transform, and estimation method, e.g. pseudo-inverse method, smooth pseudo-inverse method, Wiener estimation method, nonlinearity method, principal component analysis, independent component analysis or non-negative matrix factorization. Estimation method is usually based on known knowledge on types of spectrum found in a series of measurement in the past, i.e. training set.

In the present invention, Wiener estimation method or pseudo-inverse calibration is used to conduct spectral reflectance reconstruction. This belongs to the category of background technology, detailed descriptions of which are known to a skilled in the art and can be found in relevant publications, not to be introduced here.

Finally, after reflectance reconstruction, image data after calibration can be used for measuring color spectrum at each point of the object being measured, which gives a highly photometric accuracy.

Although this invention is described through detailed embodiments, technicians in this filed should comprehend that, without exceeding the limits of this invention, various types of transformation and equivalent substitutions to this invention are feasible. In addition, for specific condition or material, any modifications made to this invention without exceeding the limits of this invention are acceptable. Therefore, this invention is not confined to the publicized embodiments but should comprise all embodiments within the range of this invention's claims.

The invention claimed is:

1. A multispectral imaging color measurement system comprising a dark room of a confined space for multispectral imaging, a sample platform located in said dark room for laying and fastening an object being measured, an imaging device for capturing said object being measured, a controllable illumination device, a filter wheel unit, an imaging signal processing unit and an electronic control unit;

said controllable illumination device being located in the dark room comprising at least two lighting tubes arranged symmetrically above the object while pointing towards the object;

said filter wheel unit being located between said imaging device and said object for filtering light emitted from said controllable illumination device and reflected by said object;

said imaging signal processing unit is located within said imaging device for calibrating and reconstructing reflectance of images captured by said imaging device;

said electronic control unit, having communication connections with said controllable illumination device, said filter wheel unit and said imaging device, is for controlling said controllable illumination device, said filter wheel unit and said imaging device when in operation;

wherein said lighting tube comprises one or more light sources that are connected sequentially, one or more optical integrated columns for collecting maximal uniform light, a series of lenses for improving lighting uniformity and magnification, a photo-resistant plate for reducing diffused light, and wherein internal part of said lighting tube is coated with light-absorbing material for reducing internal diffused light;

said one or more light sources is selected from a halogen tungsten lamp with a smooth curve of spectral energy distribution and powered by two high-precision DC power supply;

said one or more optical integrated columns have hollow horn-like structures surrounded by a glass wall;

said series of lenses comprises optical grating for limiting light beam edges and one or more convex lenses and concave lenses having different refractive indexes; and said photo-resistant plate is located on the front edge of said series of lenses.

2. The multispectral imaging color measurement system according to claim 1, wherein said filter wheel unit comprises a step motor, a filter wheel and a belting device connecting said step motor and said filter wheel;

said step motor provides said filter wheel with power and communication for selecting position of filters, and said step motor is controlled by said electronic control unit;

said filter wheel comprises a chassis, one or more slots and one or more holes for reducing rotational mass, wherein the filters are fastened in said one or more slots through one or more upper retaining rings, and the filter wheel comprises a built-in infrared optical switch for position detection;

said belting device comprises a first synchronizing wheel mounted on rotating shaft of said step motor, a second synchronizing wheel mounted on shaft of said chassis, and a belt of said belting device meshes outer edges of the first and second synchronizing wheels.

3. The multispectral imaging color measurement system according to claim 1, wherein said imaging device further comprises a CCD sensor or a CMOS sensor, said sensor comprises a built-in A/D converter for converting light signal of selected wavelength into digital signal and generating multi-channel spectral images, wherein said light signal of selected wavelength is selected by said filter wheel unit and projected to focal plane of said sensor.

4. The multispectral imaging color measurement system according to claim 1, wherein said electronic control unit comprises an illumination device control unit for adjusting a set value of voltage and current of a power supply for said illumination device in order to keep stable operation of said one or more light sources;

a microprocessor module for controlling acceleration, steady driving and deceleration of a step motor;

an interface circuit board to enable said imaging device, illumination device control unit and filter wheel device to communicate with each other.

5. An imaging signal processing method comprising:

correcting geometric error caused by optical lens or filters;

correcting brightness of imaging signal in each optical channel;

estimating an exposure time of a linear working range for a sensor, setting said sensor to operate within said exposure time to convert incident light signal into digital imaging signal;

correcting image noise caused by inherent noise source in said sensor;

calibrating multi-channel images in the optical channels that are captured through different filters to eliminate offset of content caused by relative misaligned position of the filters in the filter wheel unit, differences in refractive indexes in the filters, a slight objective distance shift between the filters in the filter wheel unit and the object being measured;

correcting overlapping imaging signal caused by overlapping effect in each channel; and reconstructing reflectance of the imaging signal; and generating a spectral reflectance image of the object being measured;

wherein the inherent noise source comprises a dark current and said calibrating step is represented by the following formula:

$$I_{Corr}(i,j) = k \frac{I_{rep}(i,j) - I_{Dark}(i,j)}{I_{white}(i,j) - I_{Dark}(i,j)},$$

wherein $I_{Corr}$ represents a corrected image, $I_{rep}$ represents an initial or original image without correction, $I_{Dark}$ represents a dark current image, $I_{white}$ represents an uniform white target image, coefficient k is a calibration constant to guarantee that the sensor work in the linear range.

6. The method for processing imaging signals according to claim 5, wherein said calibrating multi-channel images in the optical channels that are captured through different filters further comprises:

selecting an image in a channel as a reference channel image;

calibrating images in other target channels according to the selected reference channel image;

conducting a binary preprocessing of the calibrated images collected from each channels;

extracting characteristic edges of the calibrated images collected from each channels using an edge detection algorithm;

dividing said reference channel image and target channel images into a series of local regions;

selecting a minimum value of an error cost function of spatial displacement;

determining a maximum correlation coefficient of distortion vector in each local region according to a gradient descent algorithm;

conducting a bilinear interpolation in the target images except the edges of the target images to generate offset vectors of pixels in the local regions, followed by combining said offset vector of pixels in the local regions and the offset vector of the edges of corresponding local regions to generate an offset vector group which has the same offset vector as that of an original image in the selected local region such that a mapping function f(x) is generated;

conducting a recovery calibration for said target channel images according to the mapping function f(x).

7. The method for processing imaging signals according to claim 5, wherein said correcting overlapping images caused by overlapping effect in each channel further comprises:

extracting white objects by using an image threshold process; matching each pixel of the entire image being processed with a template by scanning, determining position of overlapping images caused by overlapping effect; and eliminating the overlapping effect in the overlapping images in each imaging channel according to corresponding parameters.

8. The method for processing imaging signals according to claim 5, wherein said reconstructing reflectance of the imaging signal comprises reconstructing reflectance using Wiener Estimation Method or Pseudo Inverse Calibration.

9. An imaging signal processing method comprising:

correcting geometric error caused by optical lens or filters;

correcting brightness of imaging signal in each optical channel;

estimating an exposure time of a linear working range for a sensor, setting said sensor to operate within said exposure time to convert incident light signal into digital imaging signal;

correcting image noise caused by inherent noise source in said sensor;

calibrating multi-channel images in the optical channels that are captured through different filters to eliminate offset of content caused by relative misaligned position of the filters in the filter wheel unit, differences in refractive indexes in the filters, a slight objective distance shift between the filters in the filter wheel unit and the object being measured;

correcting overlapping imaging signal caused by overlapping effect in each channel; and reconstructing reflectance of the imaging signal; and generating a spectral reflectance image of the object being measured;

wherein said calibrating multi-channel images in the optical channels that are captured through different filters further comprises:

selecting an image in a channel as a reference channel image;

calibrating images in other target channels according to the selected reference channel image;

conducting a binary preprocessing of the calibrated images collected from each channels;

extracting characteristic edges of the calibrated images collected from each channels using an edge detection algorithm;

dividing said reference channel image and target channel images into a series of local regions;

selecting a minimum value of an error cost function of spatial displacement;

determining a maximum correlation coefficient of distortion vector in each local region according to a gradient descent algorithm;

conducting a bilinear interpolation in the target images except the edges of the target images to generate offset vectors of pixels in the local regions, followed by combining said offset vector of pixels in the local regions and the offset vector of the edges of corresponding local regions to generate an offset vector group which has the same offset vector as that of an original image in the selected local region such that a mapping function f(x) is generated;

conducting a recovery calibration for said target channel images according to the mapping function f(x).

10. The method for processing imaging signals according to claim 9, wherein said correcting overlapping images caused by overlapping effect in each channel further comprises:
extracting white objects by using an image threshold process; matching each pixel of the entire image being processed with a template by scanning, determining position of overlapping images caused by overlapping effect; and eliminating the overlapping effect in the overlapping images in each imaging channel according to corresponding parameters.

11. The method for processing imaging signals according to claim 9, wherein said reconstructing reflectance of the imaging signal comprises reconstructing reflectance using Wiener Estimation Method or Pseudo Inverse Calibration.

12. An imaging signal processing method comprising:
correcting geometric error caused by optical lens or filters;
correcting brightness of imaging signal in each optical channel;
estimating an exposure time of a linear working range for a sensor, setting said sensor to operate within said exposure time to convert incident light signal into digital imaging signal;
correcting image noise caused by inherent noise source in said sensor;
calibrating multi-channel images in the optical channels that are captured through different filters to eliminate offset of content caused by relative misaligned position of the filters in the filter wheel unit, differences in refractive indexes in the filters, a slight objective distance shift between the filters in the filter wheel unit and the object being measured;
correcting overlapping imaging signal caused by overlapping effect in each channel; and reconstructing reflectance of the imaging signal; and
generating a spectral reflectance image of the object being measured;
wherein said correcting overlapping images caused by overlapping effect in each channel further comprises:
extracting white objects by using an image threshold process; matching each pixel of the entire image being processed with a template by scanning, determining position of overlapping images caused by overlapping effect; and eliminating the overlapping effect in the overlapping images in each imaging channel according to corresponding parameters.

13. The method for processing imaging signals according to claim 12, wherein said reconstructing reflectance of the imaging signal comprises reconstructing reflectance using Wiener Estimation Method or Pseudo Inverse Calibration.

\* \* \* \* \*